US012259382B2

(12) United States Patent
Lee

(10) Patent No.: US 12,259,382 B2
(45) Date of Patent: Mar. 25, 2025

(54) ANTIGEN DETECTION METHOD AND KIT WITH FALSE POSITIVE SIGNAL REMOVED

(71) Applicant: JL MEDILABS, INC, Cheongju-si (KR)

(72) Inventor: Jong Jin Lee, Cheongju-si (KR)

(73) Assignee: JL MEDILABS, INC, Cheongju-si (KR)

( * ) Notice: Subject to any disclaimer, the term of this patent is extended or adjusted under 35 U.S.C. 154(b) by 247 days.

(21) Appl. No.: 17/560,074

(22) Filed: Dec. 22, 2021

(65) Prior Publication Data
US 2022/0205985 A1 Jun. 30, 2022

(30) Foreign Application Priority Data

Dec. 30, 2020 (KR) .......................... 10-2020-0187548

(51) Int. Cl.
G01N 33/53 (2006.01)
G01N 21/64 (2006.01)
G01N 33/542 (2006.01)

(52) U.S. Cl.
CPC ..... G01N 33/5306 (2013.01); G01N 21/6428 (2013.01); G01N 33/542 (2013.01); G01N 2021/6439 (2013.01); G01N 2458/10 (2013.01); G01N 2470/06 (2021.08)

(58) Field of Classification Search
CPC .... G01N 33/50; G01N 21/64; G01N 33/5306; G01N 21/6428; G01N 33/542; G01N 2021/6439; G01N 2458/10; G01N 2470/06; G01N 33/54393; G01N 33/582;
(Continued)

(56) References Cited

U.S. PATENT DOCUMENTS 6,228,592 B1 * 5/2001 Tsuji ................... C12Q 1/6818
536/23.1
8,445,293 B2 5/2013 Babu et al.
(Continued)

FOREIGN PATENT DOCUMENTS

EP 2670860 B1 * 8/2017 .......... C12Q 1/6804
KR 20110005025 U 5/2011
KR 20130102688 A 9/2013
(Continued)

OTHER PUBLICATIONS

Sapkota, K et al. FRET-Based aptasensor for the selective and sensitive detection of lysozyme. Sensors, 20,914.( Feb. 9, 2020 ). (Year: 2020).*
(Continued)

*Primary Examiner* — Christopher L Chin
*Assistant Examiner* — Ellis Lusi
(74) *Attorney, Agent, or Firm* — STIP Law Group, LLC

(57) ABSTRACT

A kit for detecting an antigen from which false positive signals are removed is provided. The kit includes a substrate; a capture antibody attachable onto the substrate and having a capture strand labeled with a fluorescent material; a detection antibody having a detection strand labeled with a fluorescent material and complementary to some or all of a base sequence of the capture strand; and a blocking strand having a base sequence capable of complementary binding to the capture strand or the detection strand to prevent the detection strand and the capture strand from complementary binding to each other.

11 Claims, 6 Drawing Sheets

(58) Field of Classification Search
CPC ....... G01N 33/54306; G01N 33/54373; C12Q 1/6804; C12Q 2563/107
USPC ........................................................ 436/537
See application file for complete search history.

(56) References Cited

U.S. PATENT DOCUMENTS

| | | | |
|---|---|---|---|
| 2003/0190760 | A1 | 10/2003 | Watkins et al. |
| 2014/0248710 | A1* | 9/2014 | Heyduk ............... G01N 33/542 436/501 |

FOREIGN PATENT DOCUMENTS

| | | | | |
|---|---|---|---|---|
| KR | 20140011760 | A | | 1/2014 |
| KR | 20140121221 | A | | 10/2014 |
| KR | 20160039229 | A | | 4/2016 |
| KR | 20170096619 | A | | 8/2017 |
| KR | 20180130654 | A | | 12/2018 |
| WO | WO-2013177046 | A1 | * | 11/2013 ........... C12Q 1/6804 |
| WO | WO-2015175856 | A1 | * | 11/2015 ........... C12Q 1/6832 |
| WO | WO-2019089846 | A1 | * | 5/2019 ............. C12N 15/10 |

OTHER PUBLICATIONS

Machinek, R. Control and observation of DNA nanodevices. University of Oxford (2014). (Year: 2014).*

Fiorini, F et al. Human Upf1 is a highly processive RNA helicase and translocase with RNP remodeling activities. Nature Communications, 6:7581 (2015). (Year: 2015).*

Sekar et al. Fluorescence resonance energy transfer (FRET) microscopy imaging of live cell protein localizations. J Cell Biol. Mar. 3, 2003;160(5):629-33. (Year: 2003).*

Alexander Gust et al, A Starting Point for Fluorescence-Based Single-Molecule Measurements in Biomiolecular Research, Molecules, 2014, vol. 19, pp. 15824-15865, Basel, Switzerland.

Jongjin Lee et al, Accelerated super-resolution imaging with FRET-PAINT, Molecular Brain, 2017, vol. 10, No. 63, pp. 1-9, BioMedCentral, London, United Kingdom.

Nina S. Deubner-Helfmann et al, Correlative Single-Molecule FRET and DNA-PAINT Imaging, Nano Letters, 2018, vol. 18, pp. 4626-4630, ACS Publications, Washington, D.C., USA.

Alexander Auer et al, Fast, background-free DNA-PAINT imaging using FRET-based probes, Nano Letters, Sep. 5, 2017, Just Accepted Manuscript • DOI: 10.1021/acs.nanolett.7b03425, ACS Publications, Washington, D.C., USA.

Ralf Jungmann et al, Multiplexed 3D cellular super-resolution imaging with DNA-PAINT and Exchange-PAINT, Nature Methods, Mar. 2014, vol. 11, No. 3, pp. 313-321, Nature America, Inc. New York, USA.

Ankur Jain et al, Probing cellular protein complexes using single-molecule pull-down, Nature, May 26, 2011, vol. 473, pp. 484-488, Macmilan Publishers Limited, New York, USA.

Zhengyang Zhang et al, Ultrahigh-throughput single-molecule spectroscopy and spectrally resolved super-resolution microscopy, Nature Methods, 2015, Advance Online publication, pp. 1-6, Nature America, Inc. New York, USA.

Ricardo Lamy et al, Comparative Analysis of Multiplex Platforms for Detecting Vitreous Biomarkers in Diabetic Retinopathy, TVST, Sep. 2, 2020, pp. 1-11, vol. 9, No. 10, Article 3, Association for Research in Vision and Ophthalmology, Rockville, Maryland, USA.

Stefan Pellenz, ELISA methods, Direct Assay, Indirect Assay, Sandwich Assay, Competitive Assay, An introduction to ELISA (Part 2), Antibodies Online, Retrieved on Jul. 24, 2024, pp. 1-4, Limerick, USA, https://www.antibodies-online.com/resources/17/1464/an-introduction-to-elisa-part-2/.

* cited by examiner

ANTIGEN DETECTION METHOD AND KIT WITH FALSE POSITIVE SIGNAL REMOVED

CROSS-REFERENCE TO RELATED APPLICATIONS

This application claims the priority of the Korean Patent Applications NO 10-2020-0187548 filed on Dec. 30, 2020, in the Korean Intellectual Property Office, the disclosure of which is incorporated herein by reference.

BACKGROUND

Technical Field

The present invention generally relates to a method and a kit for detecting an antigen from which false positive signals are removed.

Background Art

In the prior-art immunoassay, a method which includes fixing an antigen in a surface of a substrate using a capture antibody, binding a detection antibody labeled with a horseradish peroxidase (HRP), or a fluorescent material to the antigen, and measuring an amount of the antigen using a change in color of a buffer by the HRP, brightness of a fluorescent material, or the like, has been often used. However, the detection antibody may bind to other sites (such as a surface of the substrate) other than the antigen through the non-specific binding. As a result, an amount of the measured antigen may be made inaccurate due to the presence of false positive signals. Such false positive signals may be ignorable when a large amount of the antigen is present in a sample, but big errors may occur when a small amount of the antigen is present for detection of viral antigens, and the like. FIG. 1 is a diagram showing problems of false positivity which may be caused in the prior-art immunoassay.

Therefore, when there is a small amount of the antigen, there is a need for development of a novel approach having high sensitivity without any false positive signals in order to reduce psychological and physical burdens of subjects upon the collection of a large amount of blood and enhance the accuracy of diagnosis.

PRIOR ART DOCUMENTS

Patent Documents (Patent Document 0001) US Patent Publication No. 20030190760 titled "Reducing nonspecific binding in immunoassays performed on polymeric solid phases" (published on Oct. 9, 2003)

(Patent Document 0002) U.S. Pat. No. 8,445,293 titled "Method to increase specificity and/or accuracy of lateral flow immunoassays" (registered on May 21, 2013)

SUMMARY OF THE INVENTION

One aspect of the present invention provides a kit for detecting an antigen from which false positive signals are removed, which includes a substrate; a capture antibody attachable onto the substrate and having a capture strand labeled with a fluorescent material; a detection antibody having a detection strand labeled with a fluorescent material and complementary to some or all of a base sequence of the capture strand; and a blocking strand having a base sequence capable of complementary binding to the capture strand or the detection strand to prevent the detection strand and the capture strand from complementary binding to each other.

Another aspect of the present invention provides a method for detecting an antigen from which false positive signals are removed, which includes: (a) preparing a capture antibody having a capture strand labeled with a fluorescent material; (b) preparing a detection antibody having a detection strand labeled with a fluorescent material and complementary to some or all of a base sequence of the capture strand; (c) allowing a blocking strand to complementarily bind to one or more of the capture strand and the detection strand; (e) attaching the capture antibody onto a substrate; (f) introducing a sample including an antigen to induce an antigen-antibody reaction among the antigen, the capture antibody, and the detection antibody; (g) removing the blocking strand to allow the detection strand to complementarily bind to the capture strand; and (h) measuring fluorescence signals generated through the binding of the detection strand to the capture strand.

BRIEF DESCRIPTION OF THE DRAWINGS

The above and other objects, features and advantages of the present invention will become more apparent to those of ordinary skill in the art by describing in detail exemplary embodiments thereof with reference to the attached drawings, in which.

DETAILED DESCRIPTION

Figure 1:
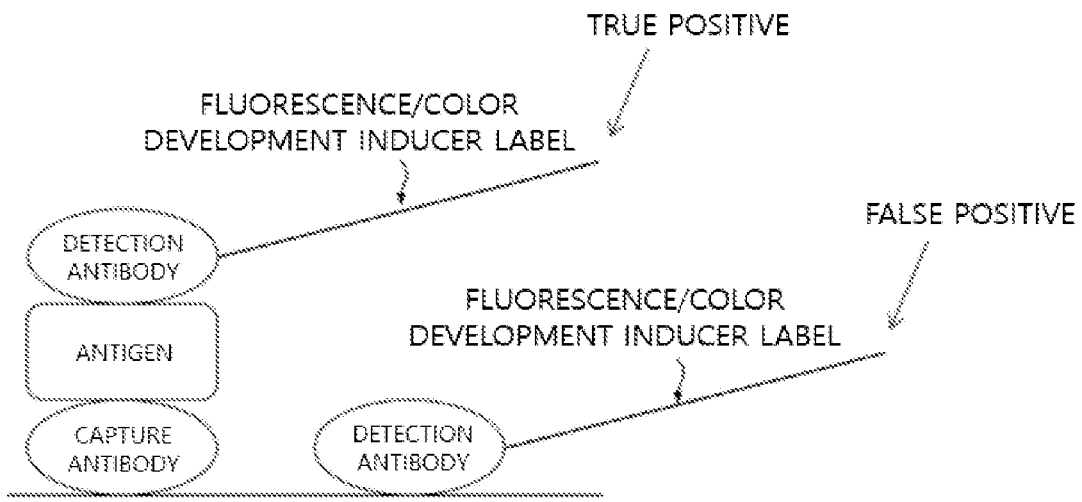
FIG. 1 is a diagram showing problems of false positivity which may be caused in the prior-art immunoassay.

Terms used in this specification will be described in brief.

In this specification, the term "biomarker" includes all types of biomaterials that may be used to check a normal or pathological condition of a living organism.

In this specification, the term "FRET" refers to a mechanism in which energy is transferred through the resonance of two adjacent fluorescent materials. Specifically, the term refers to a phenomenon in which energy of a fluorescent material excited by light is transferred to another adjacent fluorescent material, and may be intended to include all meanings of conventional FRET recognized by those skilled in the art.

In this specification, the term "FRET efficiency" means that the different energy transfer efficiency according to the distance between the fluorescent materials is represented by a value using the phenomenon in which the energy of a fluorescent material excited by light is transferred to another adjacent fluorescent material, and may be intended to include all meanings of conventional FRET efficiency recognized by those skilled in the art.

In this specification, the term "donor" refers to a fluorescent material whose energy is transferred when excited by light, that is, to a fluorescent material that absorbs or emits light with a relatively shorter wavelength when two or more fluorescent materials are adjacent to each other.

In this specification, the term "acceptor" refers to a fluorescent material that receives energy from a donor in an excited state, that is, to a fluorescent material that absorbs or emits light with a relatively longer wavelength when two or more fluorescent materials are adjacent to each other.

In this specification, the term "strand" refers to a chain of biopolymers or a chain of polymers synthesized by simulation of the biopolymers. In this case, the biopolymers may have a single-stranded or double-stranded structure, and include nucleic acids or nucleic acid analogues. The nucleic acids include deoxyribonucleic acids (DNAs) or ribonucleic acids (RNAs), and the nucleic acid analogues include peptide nucleic acids (PNAs), locked nucleic acids (LNAs), morpholino nucleic acids (MNAs), glycol nucleic acids (GNAs), threose nucleic acids (TNA), and the like.

Hereinafter, various exemplary embodiments of the present invention will be described in detail with reference to the accompany drawings. However, it should be understood that the present invention is not limited to the embodiments disclosed below, but can be implemented in various forms. Thus, all modifications, equivalents and substitutions to the exemplary embodiments are intended to fall within the scope of the present invention.

The terms used in this specification are used for the purpose of illustration only, but are not intended to limit the present invention. The singular forms "a," "an" and "the" are intended to include the plural forms as well, unless the context clearly indicates otherwise. It will be further understood that the terms "comprises," "comprising," "includes" and/or "including," when used herein, specify the presence of stated features, integers, steps, operations, elements, components and/or groups thereof, but do not preclude the presence or addition of one or more other features, integers, steps, operations, elements, components and/or groups thereof.

It will be understood that when an element is referred to as being "on" another element, it can be directly on the other element or intervening elements may be present therebetween.

As used herein, the terms (including scientific and technical terms) have the meanings commonly understood to those skilled in the art, unless otherwise indicated. In addition, it is to be understood that terms defined in commonly used dictionaries should be understood to have a consistent meaning in the context of its associated domain, and should not be interpreted as an idealized or overly formal meaning, unless otherwise clearly defined in this specification.

In addition, in describing various embodiments with reference to the accompanying drawings, a repeated description of the same elements will be omitted unless otherwise stated.

With the recent development of single-molecule fluorescence microscopic technology, molecules may be observed one by one. When this technology is applied to the detection of a biomarker, the sensitivity increases 1000-folds in units of fg/mL (Nature 473, 484-488, 2011). In the commonly used fluorescence imaging, a method of fixing a fluorescent material in a molecule to be observed and distinguishing different types of biomarkers using a fluorescence signal is used. In this case, a method of fixing fluorescent materials with different colors and distinguishing the types of biomarkers using a difference in color is used, but only 3 to 4 types of fluorescent materials may be separately observed using a conventional image sensor. Therefore, when the single-molecule fluorescence microscopic technology is used, the sensitivity increases 1,000-folds in units of fg/mL as compared to the conventional methods, but the types of biomarkers to be detected are still limited to 3 to 4.

Meanwhile, as a method of detecting various target materials at the same time while maintaining the high sensitivity of a single-molecule fluorescence microscope, FRET (Fluorescence Resonance Energy Transfer)-PAINT technology is provided as DNA-PAINT technology based on FRET. The FRET refers to a phenomenon in which energy of an excited donor is transferred to an accepto. A donor material generally emits light with a shorter wavelength than an acceptor material. In this case, the emission wavelength of the donor spectrally overlaps an excitation wavelength of the acceptor. Energy transfer rate and efficiency depend on a degree of spectral overlap between the emission wavelength of the donor and the excitation wavelength of acceptor, the quantum efficiency of the donor, a relative degree of alignment of transition dipoles of the donor and the acceptor, a distance between the donor and the acceptor, and the like.

For example, according to the FRET-PAINT technology, a docking strand may have two DNA binding sites, which may be sites for a donor strand and an acceptor strand, respectively. For single-molecule localization, a FRET signal of the acceptor is used. When the FRET-PAINT technology is used, the acceptor is not directly excited but excited by FRET to increase imager (donor and acceptor) concentrations several ten to several hundred folds. Therefore, an imaging speed may be improved several ten to several hundred folds, compared to the DNA-PAINT (Korean Patent No. 2195625).

Because the technology disclosed in this specification is also based on the FRET-PAINT technology, it is intended to provide a method and a kit for detecting an antigen with high sensitivity and accuracy. However, as mentioned in the background art, even when an antigen is detected using the FRET-PAINT technology, there are still problems regarding the false positive signals. To solve these problems, for example, a method of binding strand with fluorescent material capable of forming a FRET pair to each of a capture antibody and a detection antibody may be used. That is, because FRET may be detected only when both of the detection antibody and the capture antibody are bound to the antigen simultaneously, it may be expected that false positive signals are not generated. However, in this case, other problems of false positivity may also occur.

FIG. 2 shows that the problems of false positivity occur in a process of detecting an antigen using FRET-PAINT technology. In FIG. 2A, one or more detection strands labeled with one or more fluorescent materials are bound to the detection antibody, and one or more capture strands labeled with one or more fluorescent materials are bound to the capture antibody. Some or all of base sequences of the detection strand and the capture strand are complementary to each other. When the capture strand complementarily binds to the detection strand, a fluorescent material labeled in the detection strand and a fluorescent material labeled in the capture strand form one or more FRET pairs. Therefore, it can be seen that, when a FRET signal is detected, both of the detection antibody and the capture antibody are present at the corresponding position. FIGS. 2B and 2C shows examples of the FRET pairs formed when the capture strand complementarily binds to the detection strand. As shown in FIGS. 2B and 2C, the detection strand is preferably labeled with the fluorescent material of the donor, and the capture strand is preferably labeled with the fluorescent material of the acceptor, but the present invention is not limited thereto. Meanwhile, as shown in FIG. 2B, one fluorescent material may be used for each of the donor and the acceptor, and two or more fluorescent materials may also be used for the donor and the acceptor, as shown in FIG. 2C.

Figure 2A:
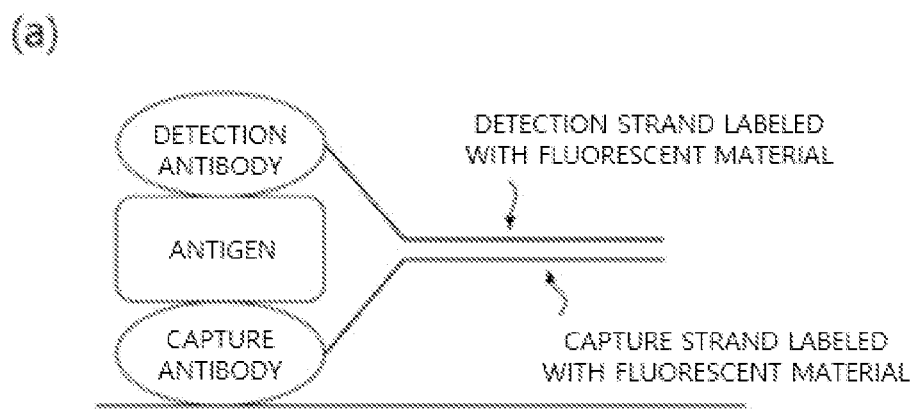
FIG. 2($a$), FIG. 2($b$), FIG. 2($c$) and FIG. 2($d$) show that the problems of false positivity occur in a process of detecting an antigen using FRET-PAINT technology.
Figure 2B:
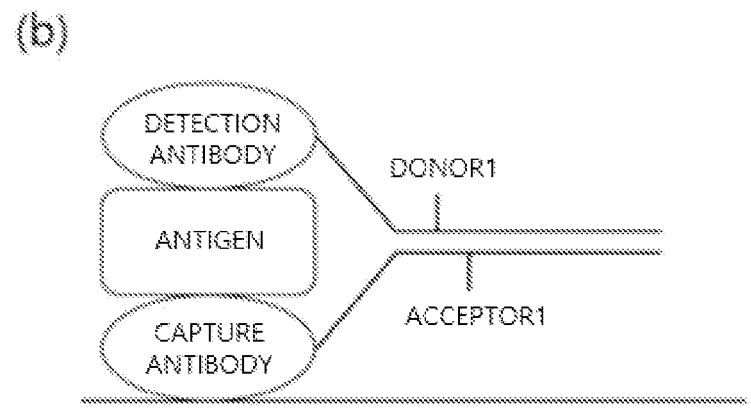
Figure 2C:
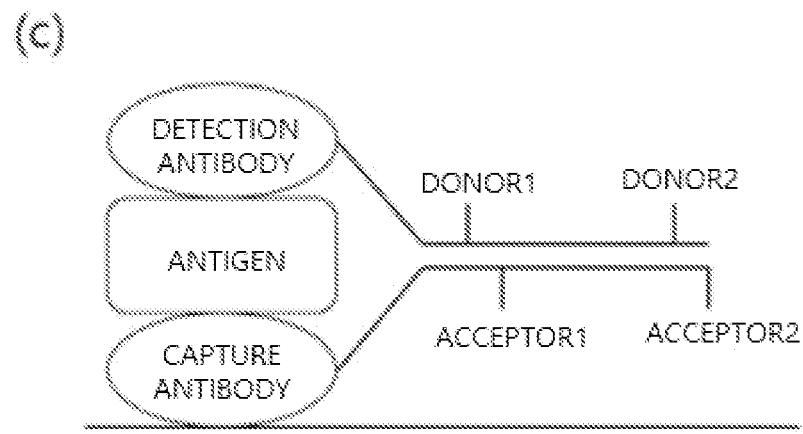
Figure 2D:
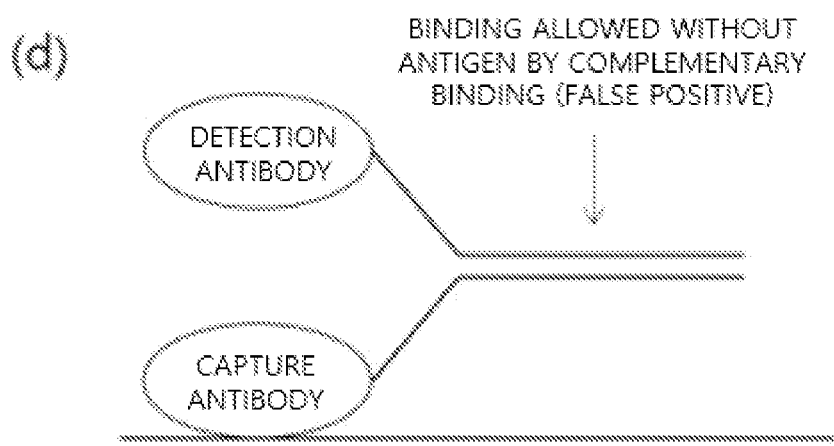

However, even when a method of observing FRET signals between the capture strand and the detection strand to detect an antigen is used, as shown in FIG. 2D, the detection strand and the capture strand may spontaneously bind to each other even without an antigen between the detection antibody and the capture antibody because the base sequences of the detection strand and the capture strand are complementary to each other, which may cause the generation of false positive signals.

Therefore, according to one aspect of the technology disclosed in this specification, there is provided a kit for detecting an antigen from which false positive signals are removed by introducing a blocking strand.

The kit for detecting an antigen includes a substrate; a capture antibody attachable onto the substrate and having a capture strand labeled with a fluorescent material; a detection antibody having a detection strand labeled with a fluorescent material and complementary to some or all of a base sequence of the capture; and a blocking strand.

The substrate is a medium used to capture and observe a target antigen. In this case, the shape of the substrate is not particularly limited, but the substrate may have a planar, spherical particle, rod-like shapes, and other atypical shapes. In this case, the substrate may also be made of glass, quartz, plastics, and the like. The substrate may be a slide glass or a cover slip in a planar shape, which is generally made of a glass material. Preferably, the substrate may be a #1 or #1.5 cover slip. The substrate may be treated with an organic material such as polyethylene glycol (PEG)-biotin in order to attach the capture antibody thereto.

The capture antibody is an antibody that may specifically bind to an antigen such as a virus or a biomarker and capture the antigen. In this case, the capture antibody may be attached to the substrate by introducing biotin to a surface of the capture antibody and introducing avidin, neutravidin, or streptavidin, which binds to the biotin, to the substrate. The detection antibody is an antibody that may specifically bind to the antigen bound to the capture antibody.

In this specification, the "antibody" used as the capture antibody and the detection antibody may specifically include monoclonal antibodies (including full-length monoclonal antibodies), polyclonal antibodies, multi-specific antibodies (for example, bispecific antibodies), and antibody fragments (for example, variable regions and other domains of antibodies exhibiting desired biological activities). In this specification, the antibody may include both of monoclonal antibodies and polyclonal antibodies, and may also include all types of chimeric antibodies, humanized antibodies, and human antibodies. Preferably, the antibody may include Fab, F (ab)2, Fab', F (ab')2, Fv, diabodies, nanobodies, or scFv. More preferably the antibody may include scFv, Fab, nanobodies, and immunoglobulin molecules. In this specification, the "antibody" includes aptamers consisting of nucleic acids, nucleic acid analogues, and peptides, which may have the same function as the antibody, because the antibody may specifically bind to a target material in addition to the immunoglobulins.

In this specification, the "strand" may have various shapes such as a general shape, a shape to which a functional group is introduced to allow the attachment of the fluorescent material, or a shape to which a fluorescent material is already attached. When the functional group is introduced into the strand, a desired fluorescent material may be attached at a desired position, and the same or different functional groups may also be attached to one strand. A distance between the donor and the acceptor varies depending on the position of the strand at which the donor and the acceptor are attached, and the FRET efficiency may also vary. The use of this nature makes it possible to detect a target antigen in a multiple detection manner.

The fluorescent material is a material that is excited by external energy such as UV rays, electric energy, heat energy, and the like to convert the energy into light, and may include an organic phosphor or an inorganic phosphor. Examples of the organic phosphor may include rhodamine, an Alexa Fluor dye, a fluorescein, fluorescein isothiocyanate (FITC), 5-carboxy fluorescein (FAM), an ATTO dye, BODIPY, a CF dye, cyanine (Cy) dye, DyLight Fluor, and Texas Red, and examples of the inorganic phosphor may include quantum dots.

When the detection strand complementarily binds to the capture strand, a fluorescent material of the capture strand and a fluorescent material of the detection strand form a FRET pair with each other. The fluorescent material of the capture strand and the fluorescent material of the detection strand may serve as a donor or an acceptor with each other on certain bases, 3'- or 5'-ends, or backbones of the capture strand and the detection strand. In this case, the FRET efficiency defined by the following equation may be measured from fluorescence signals generated from the FRET pair.

FRET efficiency=(Intensity of light emitted by acceptor)/(Sum of intensities of light emitted by donor and acceptor)

Meanwhile, the capture strand, the detection strand, and the blocking strand may be preferably nucleic acids such as DNA, RNA, PNA, LNA, MNA, GNA, TNA, or analogues thereof.

The blocking strand has a base sequence capable of complementary binding to the capture strand or the detection strand. Preferably, the blocking strand may have an additional base sequence which is not complementary to either the capture strand or the detection strand. The presence of the blocking strand may prevent the detection strand and the capture strand from complementary binding to each other. In this case, the blocking strand may be already bound to all of the capture strand, the detection strand, or the capture strand, and the detection strand.

Figure 3:
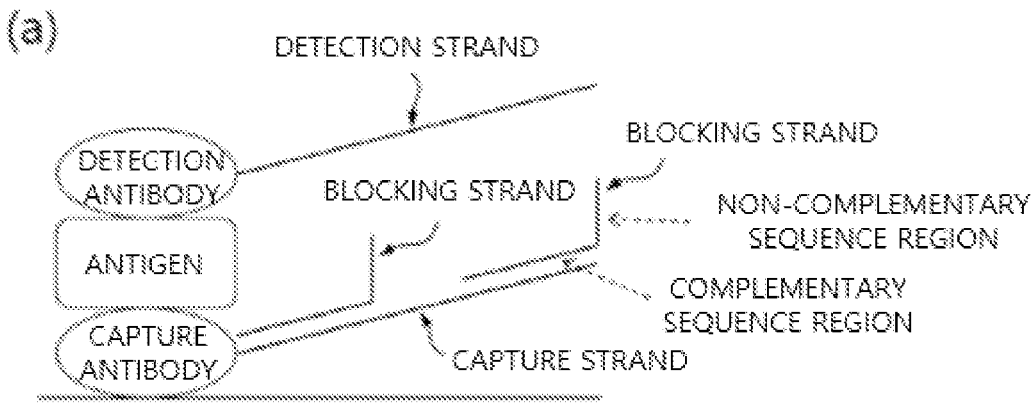
FIG. 3($a$), FIG. 3($b$) and FIG. 3($c$) show that the binding of a capture strand and a detection strand, which have a complementary sequence, is hindered by the introduction of a blocking strand.
Figure 3B:
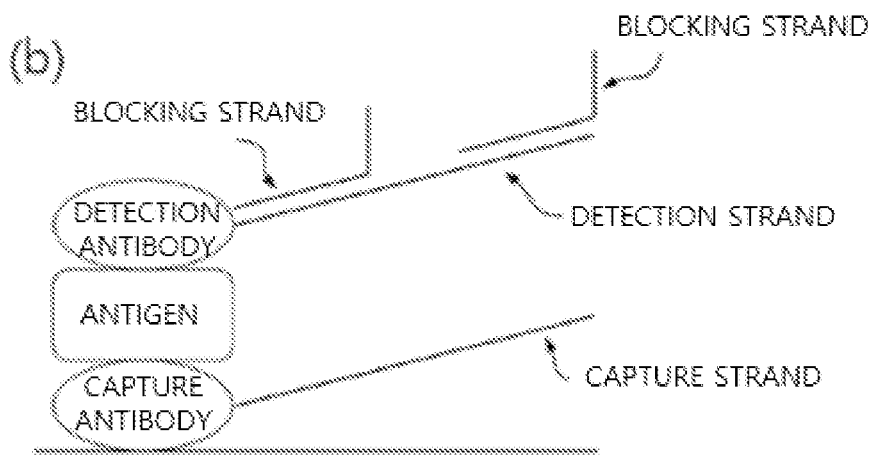
Figure 3C:
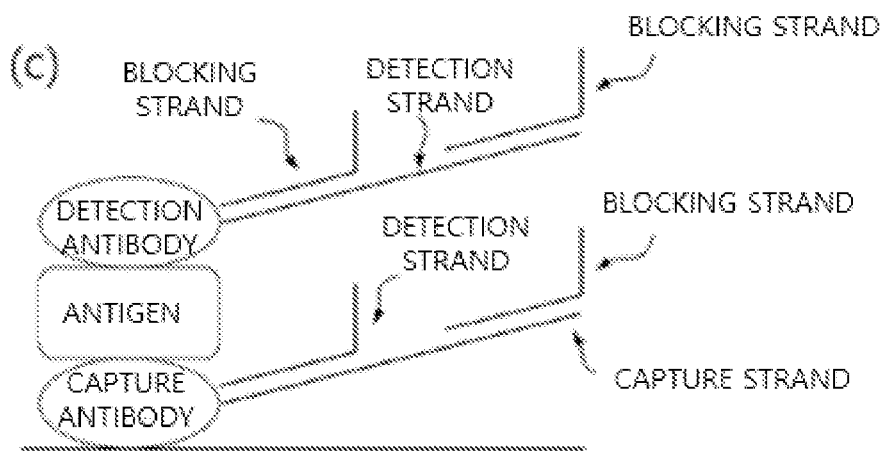

FIG. 3 shows that the binding of a capture strand and a detection strand, which have a complementary sequence, is hindered by the introduction of a blocking strand. As shown in FIG. 3, the blocking strand may be attached to any one or both of the detection strand or the capture strand.

A basic analysis procedure using the blocking strand may include: 1) fixing a capture antibody onto a surface of a substrate and washing the residual capture antibody, 2) allowing an antigen to bind to the capture antibody, and 3) allowing the detection antibody to the antigen and washing the residual detection antibody.

As shown in FIG. 3, when at least one of the detection strand and the capture strand is bound to all or some of a separate complementary strand, the detection strand and the capture strand may not stably complementarily bind to each other. As such, a separate additional strand that prevents the detection strand and the capture strand from complementary binding to each other may be referred to as a blocking strand.

Meanwhile, a portion of the blocking strand may include a base sequence which is not complementary to either the detection strand or the capture strand, and such a base sequence does not bind to these strands, and thus may be used to remove the blocking strand. The problem of false positivity may be solved by realizing the introduction of the blocking strand. Then, when the blocking strand is removed, the capture strand may complementarily bind to the detection strand to form a FRET pair.

According to one embodiment, the kit for detecting an antigen may further include a removal strand. The removal strand is complementary to the blocking strand, and serves to remove the blocking strand from the capture strand through the binding to the blocking strand.

FIG. 4 shows a process of removing a blocking strand using a removal strand. One example in which a blocking strand is bound to a capture strand is shown in FIG. 4. First, a removal strand (indicated by a dotted line) complementary to a blocking strand is injected. In this case, an exposed region of the blocking strand is sufficiently long so that it can complementarily bind to the removal strand to form a sufficient number of base pairs with the removal strand. As a result, the binding between the blocking strand and the removal strand is stable (FIG. 4A).

Figure 4A:
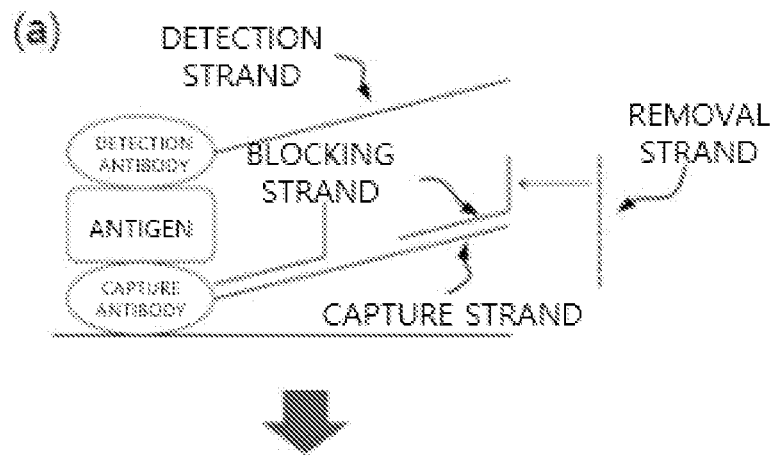
FIG. 4($a$), FIG. 4($b$), FIG. 4($c$) and FIG. 4($d$) show a process of removing a blocking strand using a removal strand.
Figure 4B:
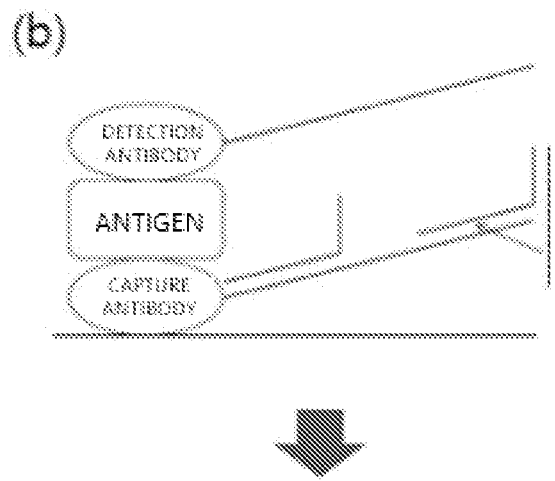

Binding of two complementary strands of a base sequence is maintained via hydrogen bonds between bases. In this case, because the hydrogen bond is a very weak bond, a bond between an end of the capture strand and the blocking strand may be intermittently broken. In this case, the removal strand may bind to the blocking strand (FIG. 4B).

Figure 4C:
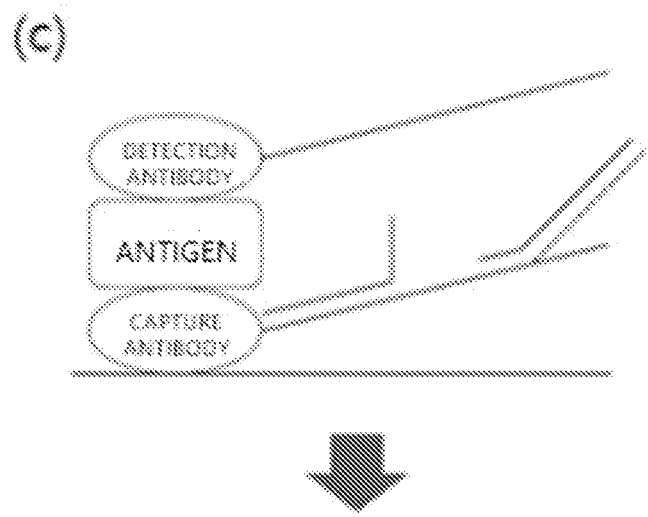

Next, when the entire removal strand is bound to the blocking strand, a portion of the blocking strand may maintain the binding to the capture strand. In this case, the number of base pairs which are complementarily bound between the blocking strand and the capture strand is not enough, which makes the bonds unstable (FIG. 4C).

Figure 4D:
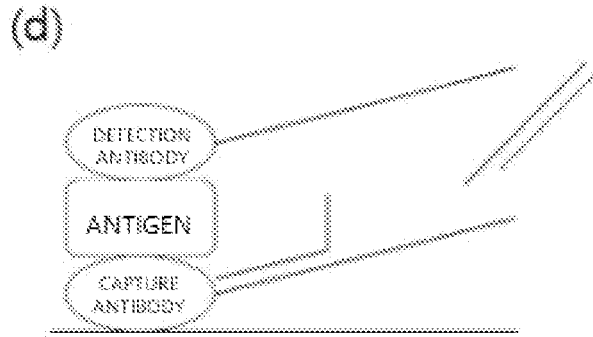

As a result, the blocking strand is detached from the capture strand to expose a region of the capture strand complementary to the detection strand, and the detection strand finally complementarily binds to the capture strand (FIG. 4D).

Because the blocking strand is complementary to the capture strand and the removal strand is complementary to the blocking strand, the removal strand has the same base sequence as the capture strand. Also, because the capture strand is complementary to the detection strand, the removal strand also has a sequence complementary to the detection strand. Therefore, the removal strand may bind to the detection strand other than the blocking strand.

Therefore, a length of the removal strand may be preferably shorter than a length of the blocking strand. The binding affinity between two strands, which are complementarily bound to each other, is in proportion to the length of the strand. Therefore, in this case, because the binding between the removal strand and the detection strand is not stable, the detection strand is detached from the removal strand in a short time even when they bind to each other, and the detection strand is maintained in a single-stranded state for a majority of time. When the removal strand binds to the blocking strand to remove the blocking strand from the capture strand, the detection strand and the capture strand may complementarily bind to each other.

The length of the removal strand is not particularly limited, and thus may vary depending on the type of materials constituting the strand, a base sequence, a ratio of guanine (G) or cytosine (C) in the base sequence, the type and temperature of a buffer, pH, a concentration of cations, and the like. In this case, the removal strand may, for example, have a length of 5 to 100 bp.

Meanwhile, according to the previous embodiments, only the removal strand may be added without any replacement of the buffer to remove the blocking strand and induce the complementary binding between the detection strand and the capture strand. However, according to other embodiments, when the buffer is used, the blocking strand may be removed without using the removal strand.

Figure 5A:
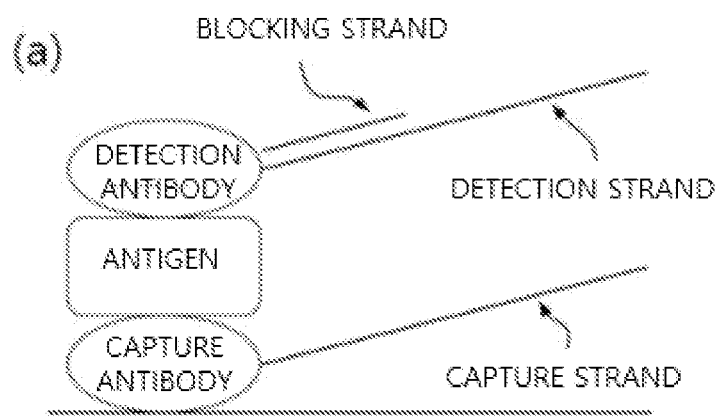
FIG. 5($a$), FIG. 5($b$) and FIG. 5($c$) show various blocking strands which form a complementary bond with a detection strand.
Figure 5B:
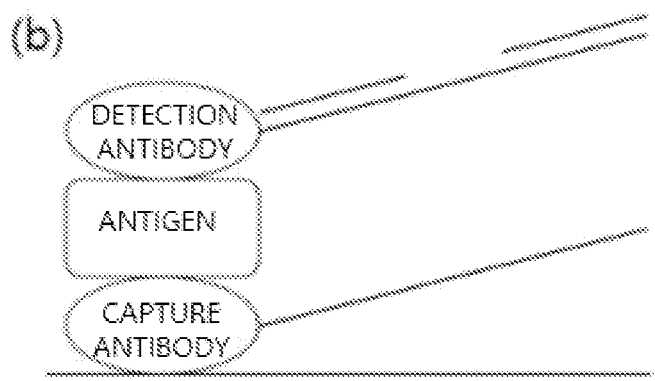
Figure 5C:
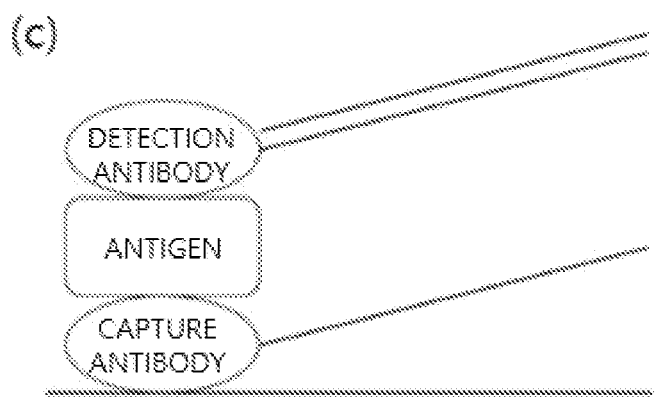

FIG. 5 shows various blocking strands which form a complementary bond with a detection strand. As shown in FIG. 5, some or all of at least one strand of either the detection strand or the capture strand is allowed to bind to the blocking strand, and an antigen-antibody reaction is then completed. Thereafter, the blocking strand may be removed without any removal strand by replacing the existing buffer with a buffer that breaks a complementary bond. Then, the capture strand may be allowed to bind to the detection strand by replacing the buffer with the previous buffer. In this case, the blocking strand has an additional base sequence which is not complementary to both of the detection strand and the capture strand, which is desirable, but it is possible that the blocking strand has no additional base sequence.

According to another aspect of this specification, there is provided a method of detecting an antigen from which false positive signals are removed by introducing a blocking strand. The method of detecting an antigen includes: (a) preparing a capture antibody having a capture strand labeled with a fluorescent material; (b) preparing a detection antibody having a detection strand labeled with a fluorescent material and complementary to some or all of a base sequence of the capture strand; (c) allowing a blocking strand to complementarily bind to one or more of the capture strand and the detection strand; (d) attaching the capture antibody onto a substrate; (e) introducing a sample including an antigen to induce an antigen-antibody reaction among the antigen, the capture antibody, and the detection antibody; (f) removing the blocking strand to allow the detection strand to complementarily bind to the capture strand; and (g) measuring fluorescence signals generated through the binding of the detection strand to the capture strand.

The binding of the blocking strand in step (c) may be performed before or after attaching the capture antibody in step (e) to the substrate.

When the capture antibody attached to the substrate is used, such an attachment may be, for example, carried out by diluting the capture antibody with a 0.06 M carbonate buffer solution or a bicarbonate buffer solution (pH 9.5) and contacting the diluted solution with the substrate at a certain temperature for a predetermined time.

Then, the capture antibody attached to the substrate forms a complex with an antigen in a specimen sample. After the formation of the complex, the complex may be preferably washed with a detergent such as a washing buffer solution (such as Tween 20), distilled water, or the like for the purpose of removing the non-specifically bound antibody or contaminants, and the like.

Types of samples are not particularly limited as long as the samples contain a target material to be detected. In this case, the sample may be a tissue, blood, serum, plasma, saliva, a mucosal fluid, urine, and the like. For example, the sample may be obtained from an animal or a human subject suspected of having a disease.

The antigen may include viruses, bacteria, nucleic acids, peptides, proteins, the endoplasmic reticulum, miRNAs, exosomes, circulating tumor cells, biomarkers, and the like. Preferably, the antigen may be a biomarker.

The technology disclosed in this specification may be used to observe cells, tissues, organs, and the like. In particular, the technology disclosed in this specification may be very effectively used to detect a biomarker in that the technology may detect various types of biomaterials through once examination to rapidly diagnose a disease at an early stage.

The biomarker may be used without any limitation as long as it is used in the conventional field of science and medicine for the measurement or evaluation of a biological treatment process, a process of inducing pathogenicity, and a pharmacological process for treatment, but the present invention is not particularly limited thereto.

For example, the biomarker may be a polypeptide, a peptide, a nucleic acid, a protein, or a metabolite, which may be detected from a biological fluid such as blood, saliva, urine, or the like. Specifically, the biomarker may include alpha-fetoprotein (AFP), CA15-3, CA27-29, CA19-9, CA-125, calcitonin, calretinin, a carcinoembryonic antigen (CEA), CD34, CD99, MIC-2, CD117, chromogranin, cytokeratin (various types: TPA, TPS, Cyfra21-1), desmin, an epithelial membrane antigen (EMA), Factor VIII, CD31, FL1, a glial fibrillary acidic protein (GFAP), a gross cystic disease fluid protein (GCDFP-15), HMB-45, human chorionic gonadotropin (hCG), immunoglobulins, inhibin, keratin (various types of keratin), a lymphocyte marker, MART-1 (Melan-A), Myo D1, muscle-specific actin (MSA), neurofilaments, a neuronspecific enolase (NSE), a placental alkaline phosphatase (PLAP), a prostatespecific antigen (PSA), PTPRC (CD45), an S100 protein, smooth muscle actin (SMA), synaptophysin, a thymidine kinase (TK), thyroglobulin (Tg), thyroid transcription factor-1 (TTF-1), M2-PK, vimentin, interleukins, CD24, CD40, integrin, cystatin, interferons, a tumor necrosis factor (TNF), MCP, VEGF, GLP, ICA, HLA-DR, ICAM, EGFR, FGF, BRAF, GFEB, FRS, LZTS, CCN, mucin, lectin, an apolipoprotein, tyrosine, a neuronal cell adhesion molecule-like protein, fibronectin, glucose, uric acid, carbonic anhydrase, cholesterol, or the like.

Also, the sample may be diluted with solution which does not include the biomarker, and a concentration of the biomarker included in the sample may differ from fg/mL to mg/mL according to the type of the biomarker. Preferably, the sample may be diluted at various ratios to detect a proper number of biomarker molecules using an image sensor. Preferably, the same sample diluted with different ratios may also be diluted. Most preferably, the sample may be diluted several times at a weight ratio of 1:10 to 1,000, and used.

A method of attaching a stand to the capture antibody or the detection antibody may be performed using a method of allowing a nucleic acid molecule to bind to a conventional protein molecule known in the art. For example, the strand may be attached by performing a binding reaction between the nucleic acid molecule and the protein molecule using a compound having two different reactive groups together. By way of one example, succinimidyl 4-(N-maleimidomethyl) cyclohexane-1-carboxylate (SMCC) has an NHS-ester group reacting with an amine and a maleimide group reacting with thiol. In this case, when a strand having a thiol group attached thereto is reacted with SMCC and the reaction product is reacted with the detection antibody, the strand is reacted with the N-terminus of the detection antibody or an amine group present in lysine to attach the strand to the detection antibody.

Meanwhile, the blocking strand is a separate additional strand that prevents the detection strand and the capture strand from complementary binding to each other, as described above. After the blocking strand is bound to the detection strand or the capture strand, the capture strand may complementarily bind to the detection strand through the removal of the blocking strand to form a FRET pair. The length of the blocking strand may be properly controlled in order to maintain the complementary binding to the detection strand or the capture strand.

The length of the detection strand or the capture strand is not particularly limited, but may be, for example, in a range of 10 to 300 bp in consideration of factors having an influence on the binding affinity, such as the type of materials constituting the strand, a base sequence, a ratio of guanine (G) or cytosine (C) in the base sequence, the type and temperature of a buffer, pH, a concentration of cations, and the like, and the number of fluorescent materials to be labeled. The length of the blocking strand may be in a range of 5 to 150 bp.

According to one embodiment, a removal strand complementary to the blocking strand may be introduced to remove the blocking strand. Here, when the removal strand is too long in length, the removal strand may stably complementarily bind to the detection strand. On the other hand, when the length of the removal strand is too short, although the removal strand complementarily binds to the blocking strand, the blocking strand may not be detached from the capture strand because the remaining region of the blocking strand is long enough to stably complementarily bind to the capture strand. The proper length of the removal strand may be properly determined depending on the type of materials constituting the strand, a base sequence, a ratio of guanine (G) or cytosine (C) in the base sequence, the type and temperature of a buffer, pH, a concentration of cations, and the like. Preferably, the length of the removal strand is desirably shorter than the length of the blocking strand in order to prevent the removal strand from stable binding to the detection strand or the capture strand.

According to another embodiment, a buffer breaking a complementary bond may be used to remove the blocking strand.

Meanwhile, the measurement of the fluorescence signals may be performed by imaging the fluorescence signals using a single-molecule microscope. A phenomenon in which energy of a fluorescent material (a donor) is transferred to another fluorescent material (an acceptor) when two different fluorescent materials are located at very close positions is referred to as FRET. When the detection strand complementarily binds to the capture strand, the fluorescent material of the capture strand and the fluorescent material of the detection strand may form a FRET pair with each other. Therefore, it can be seen that the target antigen is located at positions at which fluorescence signals are generated by the formation of the FRET pair as described above.

In conclusion, according to the above-described kit for detecting an antigen from which false positive signals are removed, and the method for detecting an antigen, it is easy to perform the multiple diagnoses, and the false positive signals may be easily removed by the exchange of the removal strand or the buffer with the introduction of the blocking strand even by using the FRET-PAINT technology with high sensitivity. Therefore, the errors may be significantly reduced, which may occur while detecting traces of various biomarkers or antigens (such as viruses, and the like) in the specimen.

Although the various embodiments have been described with reference to the accompanying drawings as described above, various technical modifications and variations are made to those skilled in the art from the detailed description.

For example, the techniques described herein may be implemented in a different order than the methods described herein, and/or components described herein may be combined or combined in different forms than the methods described herein, or other components. Or even when replaced or substituted by equivalents, appropriate results can be achieved. Therefore, other implementations, other embodiments, and equivalents to the claims fall within the scope of the claims that follow.

What is claimed is:

1. A kit for detecting an antigen from which false positive signals are removed, comprising:
   a substrate;
   a capture antibody attachable onto the substrate and having a capture strand labeled with a fluorescent material;
   a detection antibody having a detection strand labeled with a fluorescent material and complementary to some or all of a base sequence of the capture strand; and
   a blocking strand having a base sequence capable of complementary binding to the capture strand or the detection strand to prevent the detection strand and the capture strand from complementary binding to each other.

2. The kit of claim 1, further comprising a removal strand complementary to the blocking strand and capable of removing the blocking strand through binding to the blocking strand.

3. The kit of claim 2, wherein the removal strand has a shorter length than a length of the blocking strand.

4. The kit of claim 1, wherein the blocking strand further comprises an additional base sequence which is not complementary to both of the capture strand and the detection strand.

5. The kit of claim 1, wherein the fluorescent material of the capture strand and the fluorescent material of the detection strand form a FRET pair with each other when the detection strand complementarily binds to the capture strand.

6. The kit of claim 5, wherein the fluorescent material of the capture strand and the fluorescent material of the detection strand serve as a donor or an acceptor with each other.

7. A method for detecting an antigen from which false positive signals are removed, comprising:
   (a) preparing a capture antibody having a capture strand labeled with a fluorescent material;
   (b) preparing a detection antibody having a detection strand labeled with a fluorescent material and complementary to some or all of a base sequence of the capture strand;
   (c) allowing a blocking strand to complementarily bind to one or more of the capture strand and the detection strand;
   (d) attaching the capture antibody onto a substrate;
   (e) introducing a sample comprising an antigen to induce an antigen-antibody reaction among the antigen, the capture antibody, and the detection antibody;
   (f) removing the blocking strand to allow the detection strand to complementarily bind to the capture strand; and
   (g) measuring fluorescence signals generated through the binding of the detection strand to the capture strand.

8. The method of claim 7, wherein the fluorescent material of the capture strand and the fluorescent material of the detection strand form a FRET pair with each other when the detection strand complementarily binds to the capture strand.

9. The method of claim 7, wherein a removal strand complementary to the blocking strand is introduced in order to remove the blocking strand.

10. The method of claim 7, wherein a buffer breaking a complementary bond is used to remove the blocking strand.

11. The method of claim 8, further comprising the step of (h) calculating a FRET efficiency based on the fluorescence signals measured in the step (g), wherein the FRET efficiency is defined by the following equation:

$$\text{FRET efficiency} = \text{(Intensity of light emitted by an acceptor in the FRET pair)}/\text{(Sum of intensities of light emitted by a donor and the acceptor in the FRET pair)}.$$

* * * * *